United States Patent [19]
Bosker

[11] Patent Number: 5,460,526
[45] Date of Patent: Oct. 24, 1995

[54] ASSEMBLY FOR SUPPORTING A SUBMAXILLARY DENTURE ON A LOWER JAW

[76] Inventor: Hans Bosker, Essen 14, 9751 NC Haren, Netherlands

[21] Appl. No.: 210,617

[22] Filed: Mar. 18, 1994

[30] Foreign Application Priority Data

Apr. 21, 1993 [EP] European Pat. Off. ............ 93201144

[51] Int. Cl.$^6$ ................................................. A61C 8/00
[52] U.S. Cl. ............................................ 433/173; 433/172
[58] Field of Search .................................. 433/172, 173, 433/174, 176

[56] References Cited

U.S. PATENT DOCUMENTS

| | | | |
|---|---|---|---|
| 4,225,668 | 9/1980 | Bartoli | 433/176 |
| 4,906,189 | 3/1990 | Knapp | 433/173 |
| 5,221,204 | 6/1993 | Kruger et al. | 433/172 |

FOREIGN PATENT DOCUMENTS

| | | | |
|---|---|---|---|
| 0110462 | 6/1984 | European Pat. Off. | |
| 2411602 | 7/1979 | France | |
| 3736977 | 7/1988 | Germany | 433/173 |
| 2217994 | 11/1989 | United Kingdom | |
| 9004951 | 5/1990 | WIPO | |

*Primary Examiner*—Cary E. O'Connor
*Attorney, Agent, or Firm*—Ladas & Parry

[57] ABSTRACT

Assembly for supporting a submaxillary denture on a lower jaw, comprising a base plate, which has the form of a curved strip, a bridge member on which the submaxillary denture is to be placed, a set of columns which are provided with threaded bores in which fixing screws fit to connect the columns with the base plate, and which are connected with the bridge member in order to allow the base plate to support this bridge member, a set of cortical screws for securing the base plate to the lower jawbone, the base plate being provided with first holes for receiving the fixing screws for fixing the columns to the base plate and second holes for receiving the cortical screws, the first holes being formed as elongated holes, the main axis thereof extending substantially transversely to the principal direction of extension of the strip-formed base plate and the longitudinal boundaries of the elongated holes being curved convexly in a plane parallel to the longitudinal plane of symmetry of the elongated holes, and the fixing screws having a concave head which projects relative to the longitudinal boundaries of the respective elongated hole and is formed complementary thereto.

12 Claims, 3 Drawing Sheets

ASSEMBLY FOR SUPPORTING A SUBMAXILLARY DENTURE ON A LOWER JAW

The invention relates to an assembly for supporting a submaxillary denture on a lower jaw.

Such an assembly can be seen as a solution to the problem that a submaxillary denture has to be repeatedly adapted to the form of the upper side of the lower jaw, which form changes due to the reduction of the lower jaw body. This reduction is caused, among other things, by the pressure which the denture exerts on the bone tissue, in particular when biting and chewing.

An assembly of the type mentioned in the opening paragraph is known from the European Patent 110.462 in the name of Applicant, by means of which a reduction of the exerted pressure to below the critical value is brought about, by converting at least part of the chew and bite forces into a pulling force exerted on the periosteum. For this purpose the assembly comprises a base plate, which has the form of a curved strip, a bridge member, on which the submaxillary denture is to be placed, a set of columns which are connected to the base plate and to the bridge member in order to allow the base plate to support this bridge member and are fixed onto the base plate with a separate screw which reaches from the distal side through an elongated hole in the base plate intended for that purpose, in order to pull the column, which is provided with a mating threaded bore, against the base plate, and a set of cortical screws for securing the base plate to the lower jawbone, on both sides of the columns. The columns which are preferably provided with a cortical thread reduce the pressure force exerted on the bone by also transferring it to the cortical screws, which results in a pulling force on the periosteum laid back over the base plate. The external thread present on the column directly transfers part of the exerted pressure force to the bone tissue, whilst, however, applying pressure which is below the critical value. The other part of the exerted pressure force is converted into a pull force on the periosteum through the sufficiently rigid base plate.

Although this known assembly in general appears to work very satisfactorily in practise, situations can arise in which an optimal operation is not feasible.

As people get older the lower jawbone, which initially has a rounded-off L-form in cross section, will decrease in height and breadth. This can result in the columns, which project substantially vertically through the lying bone not being able to get sufficient length of engagement. Indeed, in the known assembly, in which a bevelling is realized around the elongated holes and the screw heads are correspondingly bevelled off, the columns can locally slant with respect to the base plate, but this is solely for smoothing out the form of the base plate which is twisted around the centre line. Because of the convex form of the abutting surface of the screw heads and the matching concave form of the edge areas of the respective hole in the base plate, the columns are forced into an position upright from the base plate by the force exerted by the screw on to the column.

It is an object of the present invention to improve on this, for which purpose the invention provides the assembly with the measures described in claim 1. The cortical screw portions of the columns can then engage with part of their length onto the bone tissue which is located in the stem or the upright leg of the L-form so that almost always sufficient length of engagement is given. An additional advantageous effect is that the resultant of the forces exerted by the cortical screw portions on the lower jawbone have a proximally directed component.

It is advantageous if the longitudinal edge boundaries are convex in a distal direction. Then in their inclined position the columns can engage the jawbone at more distal places.

The head of the screw of the column is preferably formed complementary to the curved longitudinal edge boundaries. By this, despite the curved form, the area of engagement of the base plate with the screw head and thus with the column can be kept large. Hereby, the screw fixes the column in a stable way in the arranged position. If the abutting surface of the screw head is concave, the stability is increased further.

It is moreover preferable that the round transverse boundaries of the elongated holes are curved in a plane which is substantially perpendicular to the longitudinal plane of symmetry of the elongated holes, having a similar sign as the longitudinal boundaries of the elongated holes. In this way the stability of the column positions in the principle direction of the base plate is promoted.

When using submaxillary dentures and support structures for that purpose, support parts will be located between the submaxillary denture and the lower jaw. These support parts are within reach of liquids and solids which are present in the mouth, such as drink and food. These substances can form deposits or can get stuck and therefore remain behind on the support structure and by doing so form a threat to the user's health. According to another aspect of the invention, care is taken to keep the surface on which deposits can occur and the number of projecting parts to a minimum. To this end the invention provides an assembly having a base plate which has the form of a curved strip, a bridge member on which the submaxillary denture is to be placed, a set of columns connected to the base plate and to the bridge member in order to allow the base plate to support this bridge member, a set of cortical screws for securing the base plate to the lower jaw-bone, the upper end of the columns being provided with a screw thread on which supporting collars are screwed which have a supporting face of the bridge member, the bridge member being composed of a number of rings interconnected by rods, each of which fit to an associated threaded end of the columns and the outer surface of which connects substantially smoothly to the peripheral edge of the supporting face of the supporting collars, and the upper side of rings being closed by washer plates which are screwed on to the threaded ends of the columns and press the ring against the supporting face and connect substantially smoothly to their outer surface to the outer surface of the rings.

An advantageous embodiment of this is one in which the washer plates are provided with through threaded bores. Through this the upper side of the rings of the bridge member may always be closed well, despite the length of the threaded end on the upper side of the columns.

In assemblies for supporting submaxillary dentures on a lower jaw, comprising a base plate, standardisation of the base plate will be aimed at, so that for this purpose only a few different embodiments will have to be made available. In some cases it could, however, be desirable to extend the base plate. If, in such cases, a separate base plate with the suitable dimensions would have to be made, then the fabrication costs would be quite high. The invention now provides for extension of the base plate by means of an extension plate. This extension plate, which is described in more detail in the claims 8 to 12, is pivotable in the principle plane of the base plate and the extension plate for setting purposes and can be secured in the desired position. The extension plate can be fixed to the base plate by means of a cortical screw or, if the submaxillary denture will extend that far, with the help of a column supporting it. In these cases not only are the forces transferred to a larger area of the lower jaw, but at the same time the plate itself serves as a form of reinforcement for the lower jaw. The extension plate can also perform this function if the area of the lower jaw concerned has been broken and for the purpose of healing must be exposed as little as possible to shearing forces.

The invention will now be described in more detail with reference to a number of exemplary embodiments shown in the accompanying drawings, in which.

Figure 1:
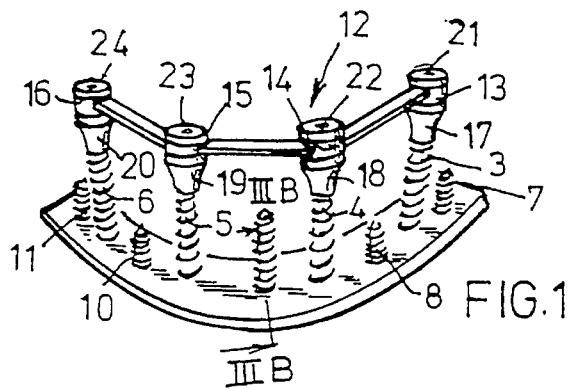
FIG. 1 shows a perspective view of an assembly to which the application refers.

In FIG. 1 the assembly for supporting a submaxilary denture on a lower jaw according to the application is shown, which assembly 1 is substantially composed of a base plate 2, columns 3–6 and bridge member 12. The assembly 1 has the appearance it would have after being mounted in the lower jaw. The parts are made of gold 18–15, i.e. 18 carat gold, alloyed with 5% platinum. This alloy is compatible with body tissue and body fluids and has the desired properties as regards workability and strength.

As opposed to the base plate discussed in the previously mentioned European Patent 110.462, here the base plate 2 has one version suitable for both adult males and adult females. The base plate is symmetrically curved to adjoin to the form of the lower edge of the jaw. Here the ends of the base plate are situated somewhat higher than the intermediate parts of the base plate.

Figure 2:
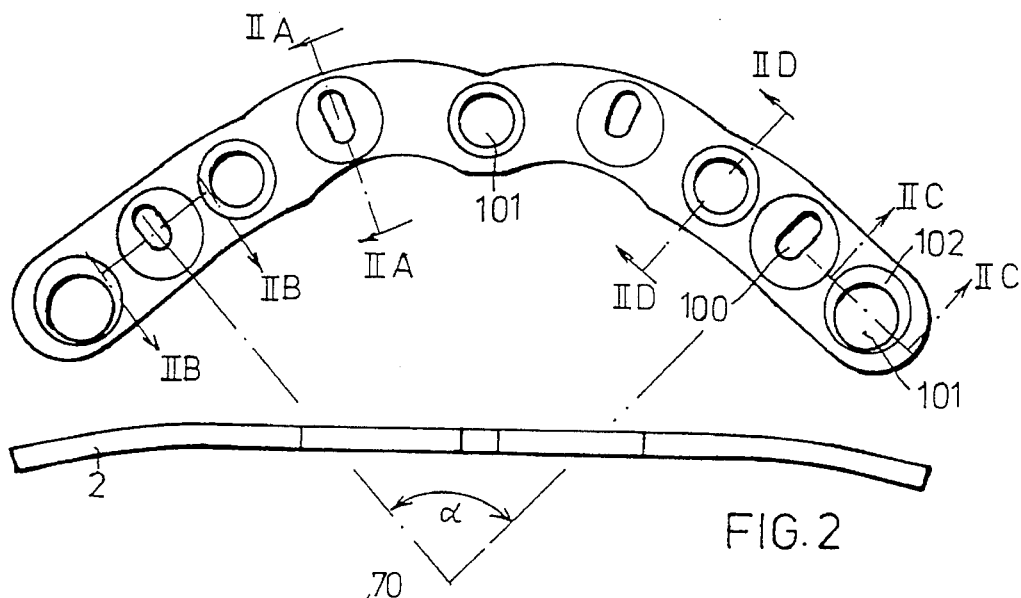
FIG. 2 shows a perspective view, from the proximal and lower side, of the base plate as well as a proximal view of it.

In FIG. 2 the base plate is shown in perspective, from the proximal side and from below, as well as in proximal view respectively. It can be seen that at both ends the base plate is bent out of the principle plane, so that in the position of use these ends are somewhat upwardly inclined. The base plate shown has a length of approx. 51 mm in proximal view, a width of approx. 7 mm, a thickness of approx. 1,5 mm, and is curved between both outer holes 100 by a radius of approx. 27 mm, concerning the distal edge, over an angle α of 2×48,5°. The distal edge is discontinuous near the centre and is slightly retracted there. At that location, the proximal edge forms concave recesses on both sides of the symmetrical plane, which are adjoined to each other by a short, straight portion.

Figure 2A:
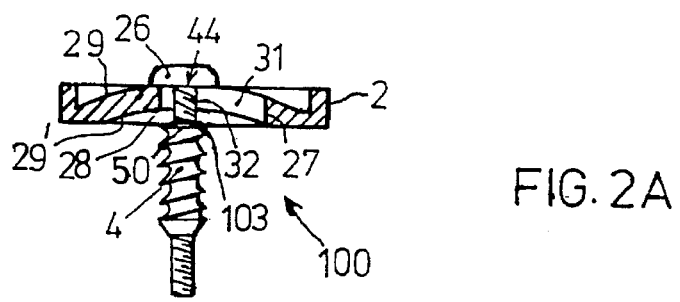
FIG. 2A shows a cross section according to IIA—IIA of the base plate of FIG. 2.
Figure 2B:
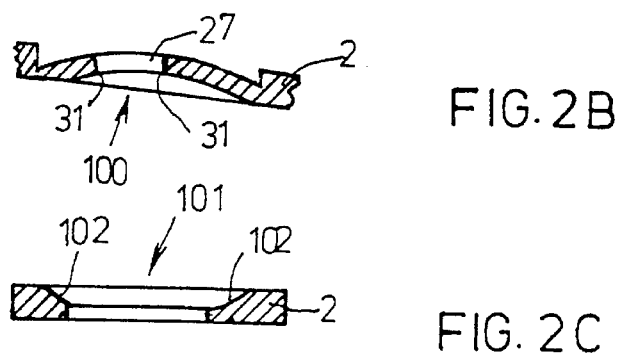
FIG. 2B shows a cross section according to IIB—IIB of FIG. 2.
Figure 2C:
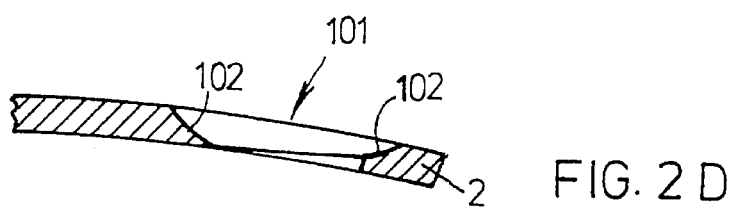
FIG. 2C shows a cross section according to IIC—IIC of FIG. 2.
Figure 2D:
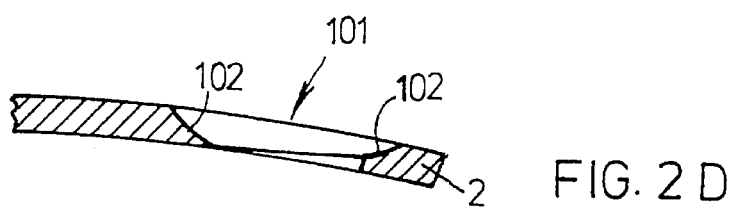
FIG. 2D shows a cross section according to IID—IID of FIG. 2.

In the FIGS. 2A and 2B cross sections are shown of holes 100 for fixing the columns and in the FIGS. 2C and 2D cross sections are shown of holes 101 for fixing the cortical screws.

At the fixing location for the cortical screws, the base plate 2 is provided with holes 101, for fixing the base plate to the lowerside of the lower jawbone, directly against the chin (corticalis refers to the hard rind of the lower jawbone that has a spongelike core). These holes allow the shank of the cortical screws 7–11 to pass with clearance but not the head thereof. In their lower area at least, the holes have a bevelled, hollow edge 102. The cortical screw heads (not shown) are formed complementarily. By this and by the clearance mentioned the cortical screws can, if desired, be screwed into the lower jaw somewhat obliquely with regard to the base plate. For this margin 102 see the cross sections according to FIGS. 2C and 2D.

At the location of the fixing positions for the column 3–6, 6, the base plate 2 is, moreover, provided with elongated holes, of which the longitudinal axis points towards the centre point of the aforementioned curve for passing the fixing screws for the columns. Like the other holes 100, the hole 100 for the fixing screw for column 4 has an elongated hole form, bounded by a downwardly convex surface 29, which merges into the remaining part of the base plate 2 at the upright, circular edge 30. As can be seen in the cross section of FIG. 2A, the elongated hole 100 is, with its centre, offset from the middle of the convex surface 29. The transverse boundary 28 of the elongated hole 100 is located near the apex of the downwardly convex surface 29 and in distal direction at a distance from there the other transverse boundary 27 is located. Just as the transverse boundaries 27 and 28, both longitudinal boundaries 31 of the elongated hole 100 have a convex course determined by the surface 29. The elongated hole 100, therefore, inclines upwardly in a distal direction. It is advantageous that the surfaces 29 and 29' have been acquired by removing material from the base plate, so that the holes 100 are more or less countersunk.

In FIG. 2A also, the fixing screw 44 is shown having a shank 32 and a head 26. The shank 32 has a left-hand thread and fits into a threaded bore 50 of column 4. The end surface 103 of the column has a curvature corresponding to the curvature of the upper or proximal surface 29'. On its abutting side facing the base plate 2, the head 26 is formed with a curvature which corresponds to the curvature of the surface 29. The surfaces 29 and 29' are complementary. This is the case in the plane of the drawing as well as in directions perpendicular thereto (see also FIG. 2B). As a result the head 26 of the screw 44 will always be able to make a surface to surface contact with the surface 29 beyond the boundaries 27, 28, 31. As a result, a transfer of large forces at the hole 100 is still possible, despite the surface of the base plate not being straight, and the chosen position of the screw 44 in relation to the base plate 2 will be stable. The curved course of the longitudinal boundaries 31 makes it possible to give the screw 44 and with that the column 4 any position desired in relation to the base plate 2, within the reach of the angle α shown in FIG. 2A, which is preferably 29°. By this the column can engage with the area of the lower jaw which will (continue to) offer sufficient material for an assured transfer of force between the column and the lower jaw. When placing the assembly through-going holes among other things are drilled into the lower jaw, in which the columns can be accommodated. The columns are then initially fixed in a loose manner onto the base plate. After the columns have been inserted into the through-holes and the base plate has been fixed to the lower jaw by the cortical screws, the columns can then be fixed in their position by tightening the fixing screws. Preceding that the columns will have been been able to adjust themselves to the direction of the through-holes.

Figure 3A:
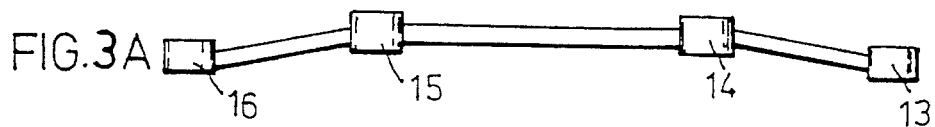
FIG. 3A shows a front view of the bridge member of the assembly of FIG. 1.
Figure 3B:
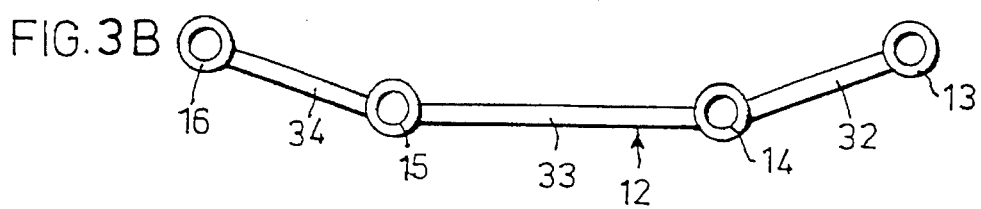
FIG. 3B shows a top view of the bridge member of FIG. 1.

In FIGS. 3A and 3B front and rear view of the bridge member 12 are shown. The bridge member 12 is composed of four rings 13, 14, 15 and 16 which are connected to each other by rods 32, 33 and 34 such that the rings 13 and 16 are situated slightly below the rings 14 and 15 and slightly proximal to them. The embodiment of the bridge member 12 shown enables it to be secured in a smoothly blending way to the ends of the columns 3, 4, 5 and 6. This is illustrated in more detail in FIG. 4. The column 5 is secured to the base plate 2 by means of a screw 35, which is concave on its side facing the base plate 2 and can therefore connect to the complementarily formed portion 57 of the respective hole in the base plate 2. As seen in the drawing in upward direction, this complementarily formed hole section 57 merges into a cylindrical section 58 in which the shank 36 of the screw 35 is incorporated. The shank 36 of the screw 35 is moreover provided with an external thread 37 which cooperates with a thread 40 in the bore 39 in the shank 38 of the column 5, which has an external cortical thread, as can be seen in the drawing. The lower end of the column 5 is convexly formed so as to be able to abut against the complementarily formed hole section 59 in the base plate 2. By means of the concave surface of the hole section 59, the concave surface of the hole section 57 and the complementarily formed surfaces of the screw 35 and the column 5 a stable orientation of the column 5 in relation to the base plate 2 is ensured.

At the upper end 42 of the column 5 an external thread 43, which cooperates with the thread 45 in bore 60 of support ring 19 is arranged. The support ring 19 has a slightly concave, frustro-conical portion 46, which forms a rather smooth transition from the outer surface of the column 5 to the portion 47 of the support ring 19 located above the column 5. The support section 47 has a substantially cylindrical outer surface but forms flat surfaces 49 on two diametrically opposing sides for engaging with a tool for screwing the support ring 19 to the end part 42. The section 47 of the support ring 19 forms a support surface 61 for the ring 15 of the bridge member 12. The ring has a bore 62, which has a diameter such that an upper, reduced portion 48 of the support ring 19 can be accommodated therein, so that the placing of the ring 15 on the support ring 44 is facilitated and the ring 15 is held against sliding in a sideward direction. A bevelling edge 63 on the lower side of the ring 15 serves as locating edge during placement of the ring 15 over the upper portion 48 of the support ring 19. A cap 23 is placed on top of the ring 15, and is composed of a lower portion 52, having a bore 53 with a thread 54, which cooperates with the thread 43 on the end part 52 of the column 5. This bore 53 is continued in the widened, upper portion 51 of the cap 23, so that, if necessary, a slight projection of the end portion 42 above the cap 23 is possible. Nevertheless, an attempt will be made to let the end portion 42 remain in one plane with the upper face of the cap 23. The ring 15 is also provided with a locating edge 64 on its upper edge for facilitating placing of the cap, with the lower part 53 in the bore 62. A corresponding construction is formed by the parts 17, 18, 20; 13, 14, 16 and 21, 22, 24 in FIG. 1. The cap 23 has a flat side portion 56.

Figure 4:
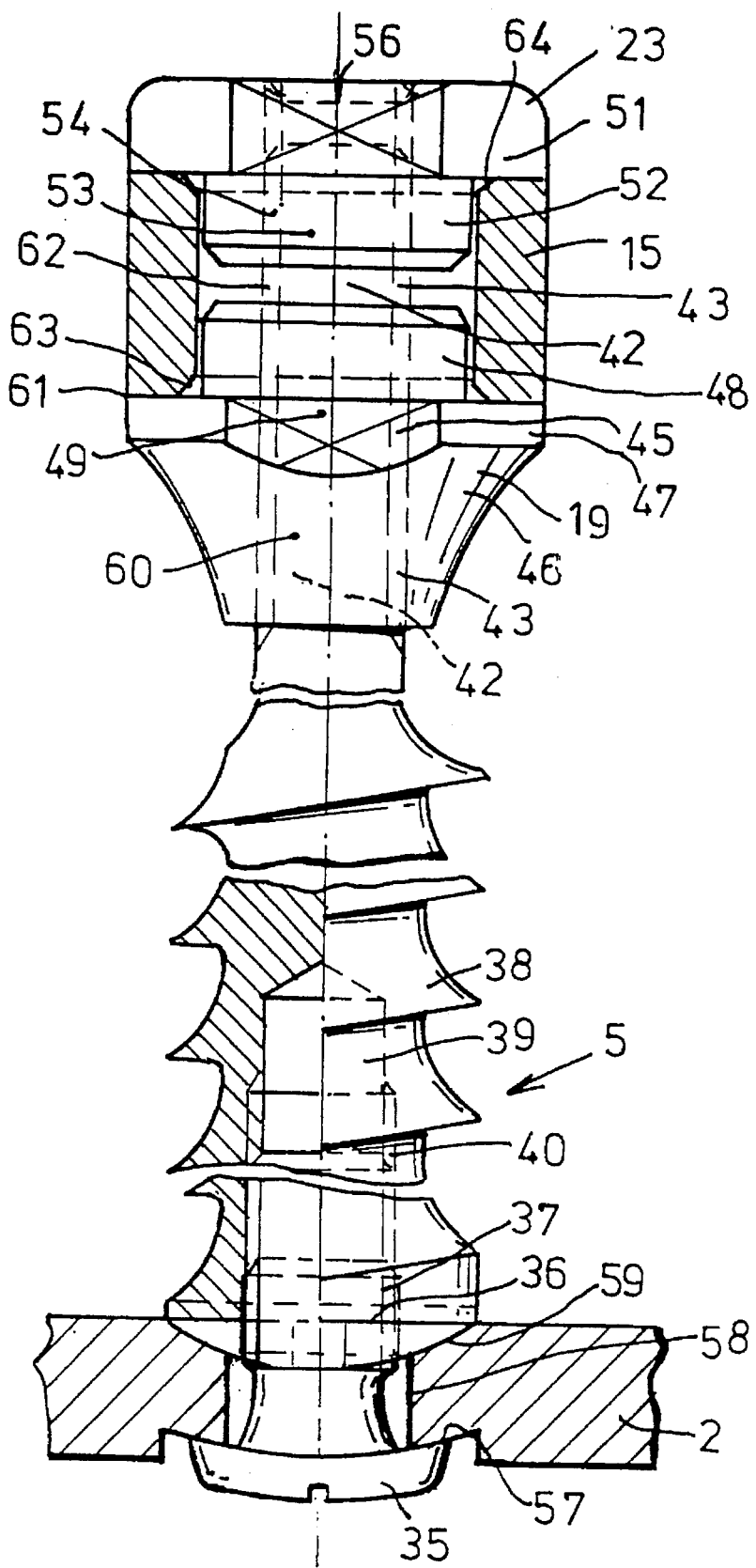
FIG. 4 shows a cross section according to IV—IV of the assembly of FIG. 1.

In FIG. 4 it can be clearly seen that the external diameters of the support ring 19, the ring 15 of the bridge member 12 and of the cap 23 are at least almost equal, so that a smooth continuous surface is acquired with a minimum of discontinuities.

When installing the denture the columns are placed first, then the base plate is arranged and the remaining screws are secured. Subsequently, the support rings are screwed to the columns after which an imprint is made for the dental technical laboratory. The loose rings of the bridge member are then placed on the model made in accordance with the imprint to then be connected to one another by the rods soldered to them. After this the completed bridge member can be fitted on the columns present in the patient, followed by screwing on the caps.

Figure 5A:
FIG. 5A shows a front view of an extension plate that can be fixed to the base plate of the assembly of FIG. 1.
Figure 5B:
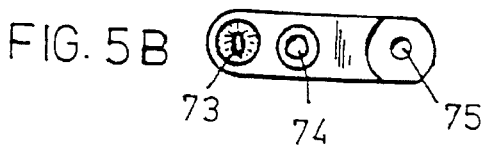
FIG. 5B shows a top view of the extension plate of FIG. 5A.
Figure 6:
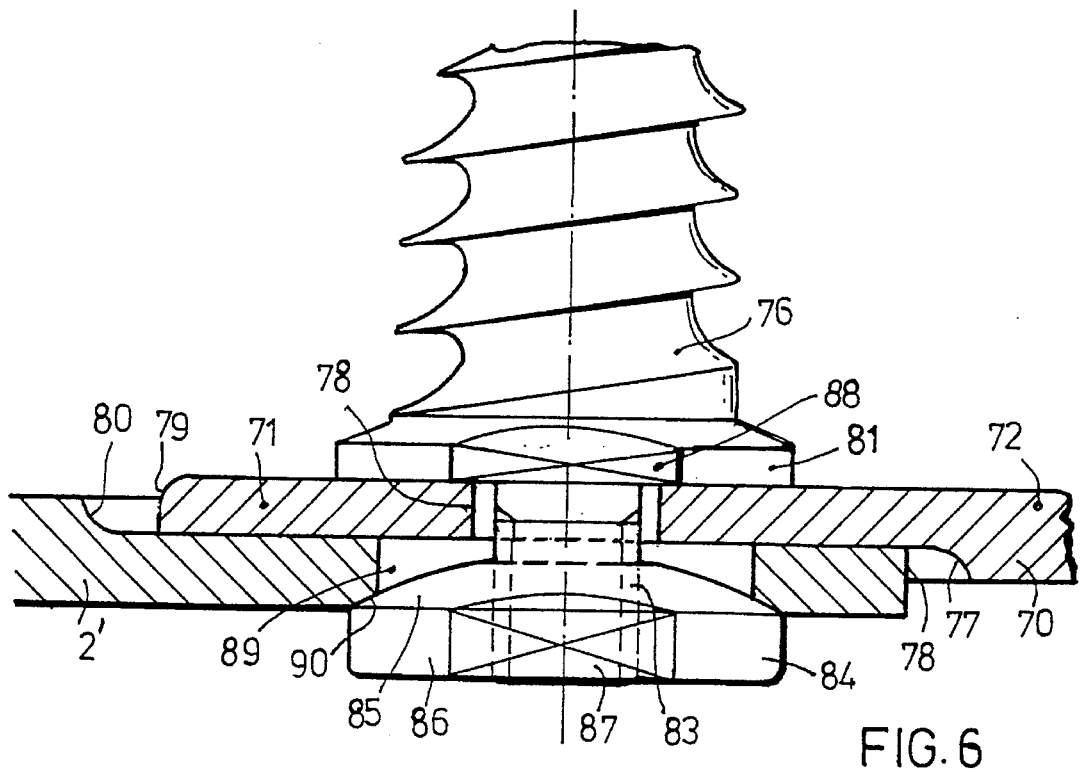
FIG. 6 shows the extension plate of the FIGS. 5A and 5B mounted on the base plate.

In the FIGS. 5A, 5B and 6, an extension plate 70 for base plate 2' is shown. The extension plate 70 can be fixed to the base plate 2' for reinforcement purposes, in case of undamaged jaws as well as broken jaws, and also to make extra space for a further column and/or cortical screw. Depending on the requirements the extension plate 70 can have one or more holes for further columns and cortical screws. The extension plate 70 shown has three holes, i.e. a hole 73 for a cortical screw, a hole 74 for a column and a hole 75 with which the extension plate 70 can be secured to the base plate 2'. For this purpose the extension plate 70 is step-formed with a thicker part 72 and a thinner part 71. With its upper face the thin part 72 can abut flatly against the lower face of the base plate 2', which is also step-formed at the end. The base plate 2' and the extension plate 70 are clamped together by means of a bolt connection with which at the same time a cortical screw 76 is fixed to the base plate. The cortical screw 76 is provided with a widened portion 81 having diametrically opposed flat sides 88 for being engaged with a tool. The widened portion 81 merges into a reduced part 82, having a thread 83. This thread end projects through the hole 75 and the hole 89, 90 in the base plate 2' to beyond the lower surface of the base plate 2'. From below a washer plate 84, the diameter of which is larger than the diameter of the hole 89, 90, projects into the hole 89, 90. The washer plate 84 also has flat, diametrically opposed faces 87 for being engaged by a tool. In upward direction, the wide part 86 of the washer plate merges into a convex frustro-conical portion 85. The surface of this portion 85 fits onto the complimentarily formed inner surface of the hole 90. Now, by almost tightening the washer plate onto the thread portion 82 of the cortical screw 76 when installing the assembly according to the invention, the extension plate 70 abuts closely against the base plate 2', a mutual rotation still being possible, however. This rotation is also made possible by the complementary circular form of the edges 77, 78 and 79, 80 of the extension plate 70 and the base plate 2', respectively. When the correct position has been found the cortical screw 76 and the washer plate 84 are screwed tightly, as a result of which the relative position of the base plate 2' and the extension plate 70 are fixed at the same time.

I claim:

1. Assembly for supporting a submaxillary denture on a lower jaw, comprising a base plate, which has the form of a curved strip, a bridge member on which the submaxillary denture is to be placed, a set of columns which are provided with threaded bores in which fixing screws fit to connect the columns with the base plate and which are connected with the bridge member in order to allow the base plate to support this bridge member, a set of cortical screws for securing the base plate to the lower jawbone, the base plate being provided with first holes for receiving the fixing screws for fixing the columns to the base plate and second holes for receiving the cortical screws, the first holes being formed as elongated holes, the main axis thereof extending substantially transversely to the principal direction of extension of the strip-formed base plate and the longitudinal boundaries of the elongated holes being curved in a plane parallel to the longitudinal plane of symmetry of the elongated holes, and the fixing screws having a head which projects relative to the longitudinal boundaries of the respective elongated hole.

2. Assembly according to claim 1, in which the longitudinal boundaries of the elongated holes are convex in the distal surface of the base plate.

3. Assembly according to claim 1, in which the transverse boundaries of the elongated holes are curved in a plane substantially perpendicular to the longitudinal plane of symmetry of the elongated holes and have a similar direction of curve as the longitudinal boundaries of the elongated holes.

4. Assembly according to claim 1, in which the head of the fixing screws is formed complementary to the curved elongated hole boundaries.

5. Assembly according to claim 1, in which the end surface of the columns facing the base plate is formed complementary to the proximal surface of the base plate, which is formed complementary to the distal surface of the base plate.

6. Assembly for supporting a submaxillary denture on a lower jaw, comprising a base plate which has the form of a curved strip, a bridge member on which the submaxillary denture is to be placed, a set of columns connected to the base plate and to the bridge member in order to allow the base plate to support this bridge member, a set of cortical screws for securing the base plate to the lower jawbone, the upper end of the columns being provided with a screw thread on which supporting collars are screwed which have a supporting face for the bridge member, the bridge member being composed of a number of rings interconnected by rods, each of which fit to an associated threaded end of the columns and the outer surface of which connects substantially smoothly to the peripheral edge of the supporting face of the supporting collars, and the upper side of rings being closed by washer plates which are screwed on to the threaded ends of the columns and press the ring against the supporting face and connect substantially smoothly to their outer surface to the outer surface of the rings.

7. Assembly according to claim 6, in which the washer plates are provided with through threaded bores.

8. Assembly for supporting a submaxillary denture to a lower jaw, comprising a base plate which has the form of a curved strip, a bridge member on which the submaxillary denture is to be placed, a set of columns connected to the base plate and to the bridge member in order to allow the base plate to support this bridge member, a set of cortical screws for securing the base plate to the lower jawbone, the base plate being provided with first holes for receiving fixing means for the columns and with second holes for receiving the cortical screws, comprising moreover a strip-formed extension piece for the base plate which is attached thereto so as to enable pivoting of the extension piece in relation to the base plate in the principal plane of the extension piece and to thereafter enable fixation the desired mutual position and in which the extension piece is provided with at least one first or second hole.

9. Assembly according to claim 8, in which the extension piece is provided with a first hole and a second hole.

10. Assembly according to claim 8, in which at the location where the extension piece is fixed the base plate a column or a cortical screw is situated.

11. Assembly according to claim 10, in which this column or cortical screw is provided with a threaded end on its distal end which reaches through the aligned holes of the extension piece and the base plate and on which a washer plate is screwed clamping the base plate and the extension piece between the washer plate and the column or the cortical screw.

12. Assembly according to claim 11, in which at the proximal side of the extension piece and the base plate the cortical screw or the column is provided with means for engaging by a tool so as to rotate the column or the cortical screw round its axis.

* * * * *